United States Patent
Malowaniec

Patent No.: US 6,242,665 B1
Date of Patent: Jun. 5, 2001

(54) BANDAGE

(75) Inventor: Krzysztof D. Malowaniec, Heidenheim (DE)

(73) Assignee: Paul Hartmann AG, Heidenheim (DE)

( * ) Notice: Subject to any disclaimer, the term of this patent is extended or adjusted under 35 U.S.C. 154(b) by 0 days.

(21) Appl. No.: 09/446,114

(22) PCT Filed: Jun. 10, 1998

(86) PCT No.: PCT/EP98/03524

§ 371 Date: Dec. 23, 1999

§ 102(e) Date: Dec. 23, 1999

(87) PCT Pub. No.: WO99/00080

PCT Pub. Date: Jan. 7, 1999

(30) Foreign Application Priority Data

Jun. 25, 1997 (DE) .............................................. 197 27 032

(51) Int. Cl.$^7$ ...................................................... A61F 13/00

(52) U.S. Cl. ................................ 602/41; 602/42; 602/46; 602/52

(58) Field of Search .................................. 602/41–49, 54, 602/56, 57

(56) References Cited

U.S. PATENT DOCUMENTS 3,885,559   5/1975   Economou .
5,088,483   2/1992   Heinecke .
5,153,040   10/1992  Faasse, Jr. .

FOREIGN PATENT DOCUMENTS 0 353 972 A1   2/1990   (EP) .
WO 93/07843   4/1993   (WO) .

Primary Examiner—Michael A. Brown
Assistant Examiner—Lalita M Hamilton
(74) Attorney, Agent, or Firm—Jones, Tullar & Cooper, P.C.

(57) ABSTRACT

The invention relates to a plaster consisting of a flat element on which an adhesive area (2) is provided. From above, said adhesive area (2) surrounds a non-adhesive area or a pad (5) on the application side. According to the invention, the adhesive area has a first sticking area (3) which surrounds the non-adhesive area or the pad (5) and a second sticking area (4) which is located outside of the first sticking area (3) and surrounds said first sticking area (3). The force of adhesion of the first sticking area (3) (0.5–2 N/25 mm) is less than that of the second sticking area (4) (2–8 N/25 mm). This ensures that the inventive plaster sticks well but can also be removed gently. The invention also relates to a plaster strip and incision plasters.

34 Claims, 1 Drawing Sheet

BANDAGE

FIELD OF THE INVENTION

The present invention relates to a bandage with a flat element on which an adhesive area is provided surrounding a non-adhesive area or a wound cover; and to a bandage strip with a strip-shaped flat element on which a non-adhesive area or a wound covering, extending in a longitudinal direction, is provided, and adhesive areas are provided on both sides of the non-adhesive area or of the wound cover, which also extend in the longitudinal direction and delimit the non-adhesive area or the wound cover transversely to the longitudinal direction when the application side is viewed from above; as well as to an incision bandage with a flat element on which an adhesive area is provided. Thus, this can be a bandage, but also a bandage strip, a post-operative wound dressing, a fixation bandage or an incision foil. As a rule, a continuous adhesive area (adhesive surface) is provided in the last mentioned two cases.

BACKGROUND OF THE INVENTION

A bandage with a wound cover and areas of different adhesiveness is known from European Patent EP-A-0 353 972.

SUMMARY OF THE INVENTION

With bandages there is a problem in that, on the one hand, they should adhere well to the skin surrounding the wound, but on the other hand they should adhere so lightly and should be removable in such a way that the previously damaged skin is gently treated. But they should also be removable causing as little pain as possible.

In accordance with the present invention, a bandage is provided with an adhesive area that comprises a first adhesive zone surrounding a non-adhesive area or a wound cover, as well as a second adhesive zone arranged outside of the first adhesive zone and surrounding it, and that at 0.5 to 2 N/25 mm, the adhesion of the first adhesive zone is less than that of the second adhesive zone of 2 to 8 N/25 mm; and to a bandage which has an adhesive area with a first, inner adhesive zone, which extends in the longitudinal direction and delimits the non-adhesive area of the wound cover, and a second outer adhesive zone extending in the longitudinal direction, and that, at 0.5 to 2 N/25 mm, the adhesive of the first adhesive zone is less than that of the second adhesive zone of 2 to 8 N/25 mm; and to a bandage which has an adhesive area with a first adhesive zone and a second adhesive zone arranged outside of the first adhesive zone, and that, at 0.5 to 2 N/25 mm the adhesion of the first adhesive zone is less than that of the second adhesive zone of 2 to 8 N/25 mm.

Advantageous further features lie in that the support for the adhesive zones comprise flat woven fabric, such as, for example, a cloth or a knit material; in that the support for the adhesive zones comprises a nonwoven material, nonwoven material lamination or a foil; in that the bandage is an incision foil or a fixation bandage; in that the support for the adhesive zones is embodied to be multi-layered and/or as a heterogeneous structure; in that the transition from a strong adhesion to a lesser adhesion is steady; in that the transition takes place as a continuous, preferably constant, gradient; in that the adhesive area as a whole comprises a first adhesive layer, and a second adhesive layer applied to the first adhesive layer in the area of the first adhesive zone or the second adhesive zone; in that the first adhesive layer has a strong adhesion and the second adhesive layer has a lesser adhesion; and in that a flat piece as a finger lift, preferably a strip of the same adhesion as that of the first adhesive zone, extends from the first inner adhesive zone of a lesser strength as far as the edge of the bandage, preferably a corner.

Thus, the outer adhesive area, i.e. the second adhesive zone applied on the edge, is provided with a greater adhesive strength. In a bandage, this adhesive zone is farther removed from the wound than the first adhesive zone, which has a lesser adhesive strength. It is therefore possible to apply a layer of greater adhesive strength in the second adhesive zone, which is sufficient for the desired good and lasting adhesion of the bandage on the skin surrounding a wound of the patient. The inner first adhesive zone can then be designed to be comparatively less adhesive. It basically only needs to assure the steady position of the bandage, and therefore the surroundings of the wound cover, for example. It is possible to assure in this way that, when being pulled off, the previously damaged skin is not stressed any more than necessary, i.e. much less than up to now, in spite of a relatively large adhesive zone.

BRIEF DESCRIPTION OF THE DRAWINGS

Three exemplary embodiments of the present invention are described in conjunction with the three drawing figures.

DESCRIPTION OF THE PREFERRED EMBODIMENTS

Figure 1:
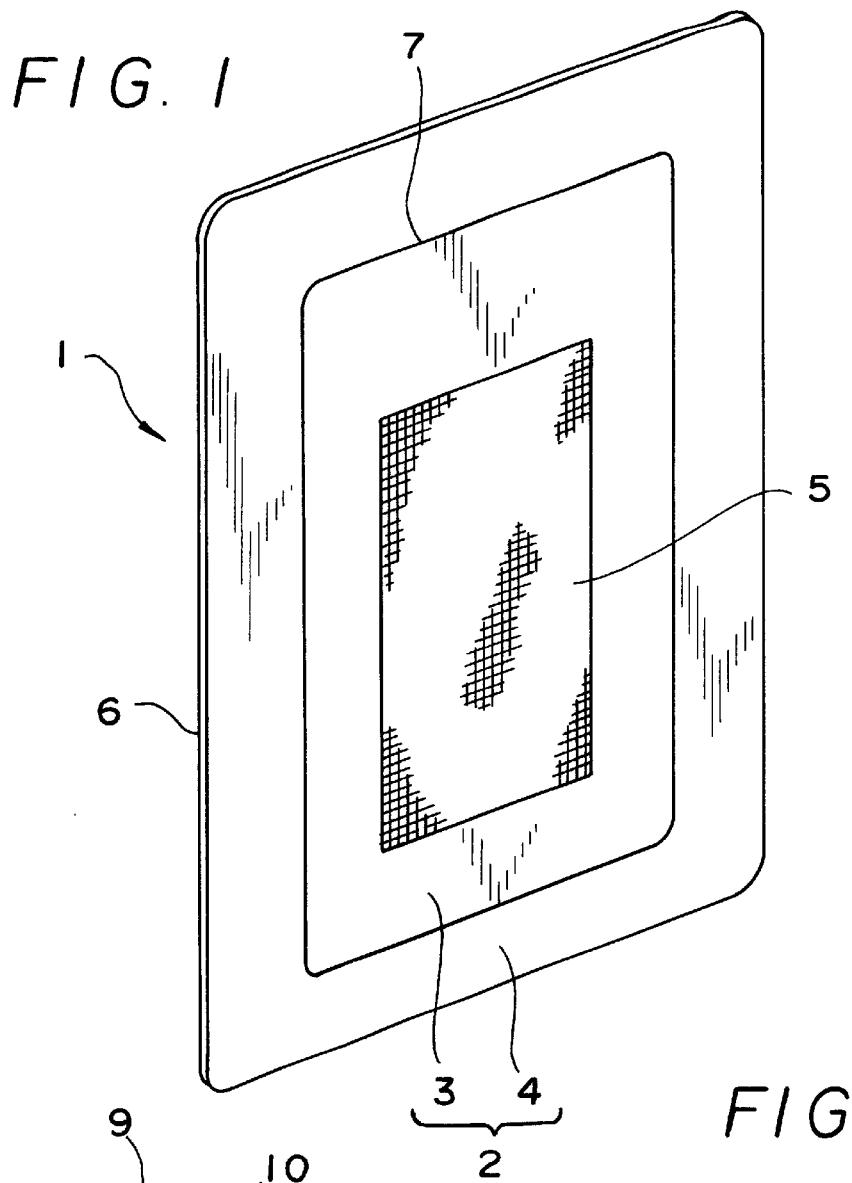
FIG. 1 is a plan view in perspective of a bandage according to one embodiment of the present invention.

FIG. 1 shows a bandage 1 having an adhesive area 2 divided into a first inner adhesive zone 3 and a second outer adhesive zone 4. The inner adhesive zone 3 directly surrounds a wound cover 5; the outer adhesive zone 4 directly surrounds the adhesive zone 3. The boundary is identified by 7. The area facing the viewer of the enclosed drawing is then customarily covered by a protective foil (not represented), which is pulled off before the bandage is applied.

The adhesive strength of the inner adhesive zone 3 is relatively weak and lies in the range between 0.5 to 2 N/25 mm. This means that a force of this size is required for removing a strip of a width of 25 mm (see the description of the testing method hereinafter). The adhesive strength of the outer second adhesive zone 4 is greater and lies in the range between 2 to 8 N/25 mm.

A support 6, on which the two adhesive zones 3, 4 and the wound cover are placed, can consist of a flat woven fabric, such as a cloth or a knit material, for example, or of a nonwoven material or a foil, which are coated, preferably continuously, with an adhesive in the usual fashion. Single layer or multi-layer, but also heterogeneous structures can be used here.

The present invention is not only used for bandages of the type represented in the drawings, but also for bandage strips, post-operative wound dressings and fixation bandages for needles, cannulae or dressings. When using the fixation bandage for a cannula a further advantage arises, in that the central area which is taken up by the wound cover 5 in the exemplary embodiment represented in FIG. 1, is left free of adhesive, so that there is no danger that the bandage will adhere too strongly to the cannula or the like which it is intended to fix in place, so that the cannula would be inadvertently pulled out when the bandage is removed or, vice versa, when the cannula is removed, that the bandage is torn off in an uncontrolled manner.

Bandages containing active ingredients (for example antirheumatic bandages) are also considered, wherein the outer adhesive zone provides the required adhesive strength and the inner adhesive zone need only adhere sufficiently for providing the skin contact required for the desired effect. These are often bandages with a quite large surface area, whose removal as a result of skin irritations, or also only as a result of body hair, can be very painful. These disadvantages are considerably reduced by means of the present invention.

So-called incision foils are also considered as an area of use. These are foils provided with an application aid, which are stuck on the skin prior to performing a surgical intervention in order to prevent an incision to spread open during an operation.

These layers constituting the two adhesive zones 3 and 4 can be applied in a known manner, for example by an appropriately clocked spray or slotted head application, or by means of screen print or rotogravure printing techniques. In connection with processing technology it can also be advantageous to first provide the entire support 6 with a strongly adhesive layer, and then to apply a second coating of a weakly adhering layer to the surface constituting the first adhesive zone 3, which is delimited by the line 7, so that the stronger adhesive layer only becomes effective in the outer adhesive zone, while it is covered by the weaker adhesive layer in the inner adhesive zone.

In regard to the adhesive strength, the transitions between the two adhesive zones can be designed to be continuous, i.e. without steps. If there is a steady transition, in particular with constant gradients, from the strongest to the least adhesion, is provided from the outer edge as far as the wound cover 5, this is also considered to fall under the provisions of the present invention.

Figure 2:
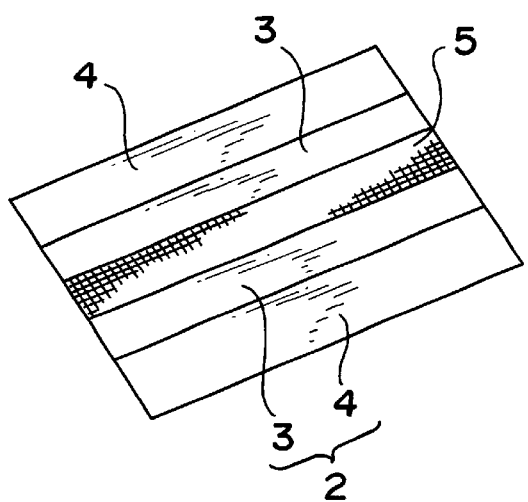
FIG. 2 is a plan view in perspective of a bandage according to a further embodiment of the present invention.

FIG. 2 shows a bandage strip which differs from the bandage in FIG. 1 in that the adhesive area 2 does not completely surround the non-adhesive area, constituted by the wound cover 5, but only transversely with respect to the longitudinal direction of the bandage strip.

Figure 3:
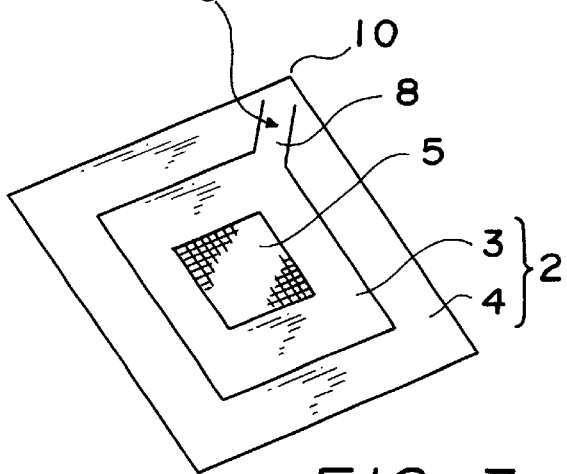
FIG. 3 is a plan view in perspective of a bandage according to a still further embodiment of the present invention.

In the exemplary embodiment in accordance with FIG. 3, the outer adhesive zone 4, which has the stronger adhesion, has a small gap in the shape of a strip 8 at the corner 7. This gap is coated with the adhesive of the adhesive zone 3 (reduced adhesion). The result is a strip 8 of the adhesive zone 3 as far as the edge of the bandage, or respectively its corner 10. The corner piece 9 being created in this way is especially suited as a finger lift for grasping when pulling off the bandage.

The repeatedly mentioned adhesive strength is measured in the following way: the force required for pulling an adhesive strip, for example a bandage, off a level surface at an angle of 90° at a constant speed is measured. For this purpose a test strip is first pre-dried for four hours at 105° C. and thereafter is stored for 20 hours in a standard environment (room temperature 23° C. and 50% humidity). Immediately prior to the test, the test material is pulled off the roll at a speed of approximately 30 cm/s. Then a strip of a length of 400 mm and of the predetermined width (for example 25 mm) is cut. With test strips having a cover paper on the back, first the cut is made, then the cover paper is removed. The sample is applied to the center of this plate with the coated side, namely parallel with the longitudinal edge of the plate. Prior to this the plate is cleaned by means of a cotton swab soaked in benzene or butyl alcohol. Then toluene is heated to boiling in a suitable container and the plate is suspended above the container in such a way that it does not come into direct contact with the liquid. Once the steam has reached the upper edge of the plate, this state is continued for five minutes. The plate is then removed and allowed to cool for approximately 30 minutes in the standard environment (see above). After the sample has been applied to the plate, it is gently smoothed by a finger for removing trapped air. Thereafter the sample is rolled by means of a tape applicator at a sample width of 20 N/cm. In i.e., the tape applicator, which comprises a roller, is pressed onto the sample strip with a force of 20 Newtons per cm of width of the strip the course of this the plate should be touched as little as possible in order to avoid warming it. For the measurement, the end of the test strip is exposed and flipped back and pulled off approximately 25 mm in front of the end of the steel plate. The plate is placed between the support surface and rollers of a testing arrangement (tensile testing machine in accordance with DIN 51221, class 1), so that it can be easily pushed. The sample end is placed between the two rollers and clamped in the upper clamp of the tensile testing machine. The draw-off angle is 90°. The draw-off speed is set to 300 mm per minute. After the measured value indicator has been reset to zero, the measurement is performed. For determining the adhesive strength, the progression of the force is recorded by a recorder or PC. The mean adhesive strength is determined from the force peaks in the following manner. If the diagram has more than twenty clearly recognizable force peaks, four vertical lines at distances of 1/10 of the diagram length are drawn in toward both sides from the center of each diagram length extending from the first force peak to the pull-off. The nine peak values which are closest to these lines are used for determining the adhesive strength. Peak values which project extremely out of the path of the curve are not considered. The result is determined as the average value of at least three tests in N/25 mm, rounded off to one place after the period, and is displayed. The adhesive force is calculated as follows:

$$F = \left(\sum_{i=1}^{n} F_i\right) / n$$

wherein $F_i$ are the force peaks $F_1, F_2, \ldots F_n$, and n is the number of force peaks considered.

What is claimed is:

1. A bandage, comprising:
   a flat element;
   a non-adhesive area mounted on said flat element;
   an adhesive area surrounding said non-adhesive area, said adhesive area mounted on said flat element,
   wherein said adhesive area includes a first adhesive zone and a second adhesive zone, situated outside and surrounding said first adhesive zone, and
   wherein at 0.5 to 2 N/25 mm, the adhesion of said first adhesive zone is less than the adhesion of said second adhesive zone at 2 to 8 N/25 mm.

2. The bandage as defined in claim 1, wherein said flat element comprises a flat woven fabric, such as one of: a cloth and a knit material.

3. The bandage as defined in claim 1, wherein said flat element comprises one of: a nonwoven material, a nonwoven material lamination and a foil.

4. The bandage as defined in claim 1, wherein the bandage comprises one of an incision foil and a fixation bandage.

5. The bandage as defined in claim 1, wherein said flat element is one of multi-layered, a heterogeneous structure, and multi-layered and a heterogeneous structure.

6. The bandage as defined in claim 1, wherein the transition from a strong adhesion to a lesser adhesion is steady.

7. The bandage as defined in claim 6, wherein the transition takes place as a continuous gradient.

8. The bandage as defined in claim 6, wherein the transition takes place as a continuous, constant gradient.

9. The bandage as defined in claim 1, wherein said adhesive area comprises a first adhesive layer and a second adhesive layer applied to the first adhesive layer in one of: the first adhesive zone and the second adhesive zone.

10. The bandage as defined in claim 9, wherein said first adhesive layer is in said second adhesive zone with strong adhesion, and said second adhesive layer is in said first adhesive zone with a lesser adhesion.

11. The bandage as defined in claim 1, further comprising:
a finger lift of the same adhesion as that of the first adhesive zone, said finger lift extending from said first inner adhesive zone of a lesser strength and as far as the edge of the bandage.

12. The bandage as defined in claim 11, wherein said finger lift comprises a strip.

13. A bandage strip, comprising:
a strip-shaped flat element;
a non-adhesive area extending in a longitudinal direction on said strip-shaped flat element; and
an adhesive layer situated on said strip-shaped flat element on either side of said non-adhesive area, extending in said longitudinal direction, said adhesive layers delimit said non-adhesive layer transversely to the longitudinal direction,
wherein said adhesive areas comprise: a first inner adhesive zone which extends in the longitudinal direction and delimits said non-adhesive area; and a second outer adhesive zone extending in the longitudinal direction, and
wherein at 0.5 to 2 N/25 mm the adhesion of said first adhesive zone is less than the adhesion of said second adhesive zone at 2 to 8 N/25 mm.

14. The bandage strip as defined in claim 13, wherein said flat element comprises a flat woven fabric, such as one of: a cloth and a knit material.

15. The bandage strip as defined in claim 13, wherein said flat element comprises one of: a nonwoven material, a nonwoven material lamination and a foil.

16. The bandage strip as defined in claim 13, wherein the bandage comprises one of: an incision foil and a fixation bandage.

17. The bandage strip as defined in claim 13, wherein said flat element is one of: multi-layered, a heterogeneous structure, and multi-layered and a heterogeneous structure.

18. The bandage strip as defined in claim 13, wherein the transition from a strong adhesion to a lesser adhesion is steady.

19. The bandage strip as defined in claim 18, wherein the transition takes place as a continuous gradient.

20. The bandage strip as defined in claim 18, wherein the transition takes place as a continuous, constant gradient.

21. The bandage strip as defined in claim 13, wherein said adhesive area comprises a first adhesive layer and a second adhesive layer applied to the first adhesive layer in one of the first adhesive zone and the second adhesive zone.

22. The bandage strip as defined in claim 21, wherein said first adhesive layer is in said second adhesive zone with strong adhesion, and said second adhesive layer is in said first adhesive zone with a lesser adhesion.

23. An incision bandage, comprising:
a flat element; and
an adhesive area mounted on said flat element,
wherein said adhesive area includes a first adhesive zone and a second adhesive zone, situated outside of said first adhesive zone, and
wherein at 0.5 to 2 N/25 mm, the adhesion of said first adhesive zone is less than the adhesion of said second adhesive zone at 2 to 8 N/25 mm.

24. The incision bandage as defined in claim 23, wherein said flat element comprises a flat woven fabric, such as one of a cloth and a knit material.

25. The incision bandage as defined in claim 23, wherein said flat element comprises one of : a nonwoven material, a nonwoven material lamination and a foil.

26. The incision bandage as defined in claim 23, wherein the bandage comprises one of : an incision foil and a fixation bandage.

27. The incision bandage as defined in claim 23, wherein said flat element is one of : multi-layered, a heterogeneous structure, and multi-layered and heterogeneous structure.

28. The incision bandage as defined in claim 23, wherein the transition from a strong adhesion to a lesser adhesion is steady.

29. The incision bandage as defined in claim 28, wherein the transition takes place as a continuous gradient.

30. The incision bandage as defined in claim 28, wherein the transition takes place as a continuous, constant gradient.

31. The incision bandage as defined in claim 23, wherein said adhesive area comprises a first adhesive layer and a second adhesive layer applied to the first adhesive layer in one of the first adhesive zone and the second adhesive zone.

32. The incision bandage as defined in claim 23, wherein said first adhesive layer is in said second adhesive zone with strong adhesion, and said second adhesive layer is in said first adhesive zone with a lesser adhesion.

33. The incision bandage as defined in claim 23, further comprising:
a finger lift of the same adhesion as that of the first adhesive zone, said finger lift extending from said first inner adhesive zone of a lesser strength and as far as the edge of the bandage.

34. The incision bandage as defined in claim 33, wherein said finger lift comprises a strip.

* * * * *